United States Patent

Maltabes et al.

[11] Patent Number: 5,885,532
[45] Date of Patent: Mar. 23, 1999

[54] BURETTE APPARATUS

[75] Inventors: Angelo John Maltabes; Godried Ferdinand Belser, both of Gladstone, Australia

[73] Assignee: Noonbeach Pty Ltd., Gladstone, Australia

[21] Appl. No.: 817,341

[22] PCT Filed: Mar. 26, 1995

[86] PCT No.: PCT/AU95/00634

§ 371 Date: May 27, 1997

§ 102(e) Date: May 27, 1997

[87] PCT Pub. No.: WO96/09845

PCT Pub. Date: Apr. 4, 1996

[30] Foreign Application Priority Data

Sep. 26, 1995 [AU] Australia ................................. PM8382

[51] Int. Cl.$^6$ ..................................................... B01L 3/02
[52] U.S. Cl. ........................ 422/100; 422/106; 422/919; 422/920; 73/863.71; 73/864.15; 436/180
[58] Field of Search .............................. 422/99, 100, 103, 422/105, 106, 919, 920; 73/863.71, 864.15; 436/180

[56] References Cited

U.S. PATENT DOCUMENTS

| 2,558,387 | 6/1951 | Ray ........................................ 73/863.71 |
| 3,207,372 | 9/1965 | Evans . |
| 3,929,157 | 12/1975 | Serur . |
| 3,949,745 | 4/1976 | Howell . |
| 3,989,043 | 11/1976 | Dimeff . |
| 4,096,879 | 6/1978 | Serur . |
| 4,256,103 | 3/1981 | Mylrea . |
| 4,449,976 | 5/1984 | Kamen . |
| 4,623,333 | 11/1986 | Fried ........................................ 604/80 |
| 5,059,173 | 10/1991 | Sacco ....................................... 604/80 |

FOREIGN PATENT DOCUMENTS

| 1098088 | 8/1989 | Australia . |
| 1511367 | 5/1978 | United Kingdom . |
| 2178135 | 2/1987 | United Kingdom . |
| 8302561 | 8/1983 | WIPO . |

Primary Examiner—Krisanne Thornton
Assistant Examiner—Fariborz Moazzam
Attorney, Agent, or Firm—Dvorak & Orum

[57] ABSTRACT

There is provided a burette apparatus having a delivery tube connecting a fluid bag to a burette assembly, via a fluid entry spigot formed in an end cap assembly of the burette assembly, the end cap assembly having a bypass spigot connected to the delivery tube and usually closed by clip, to allow an override for adding liquid to the burette. The end cap assembly closes the upper end of the transparent, cylindrical burette body, into which extends a stainless steel tube extension of the fluid entry spigot, the lower end of the burette body being closed by a lower closure assembly having a check valve and a drip chamber. An outlet tube passes from the drip chamber to the patient via regulating clamp. A float assembly is located in the burette body including an extension rod provided with a resilient cup adapted to engage the open end of the stainless steel tube extension.

18 Claims, 1 Drawing Sheet

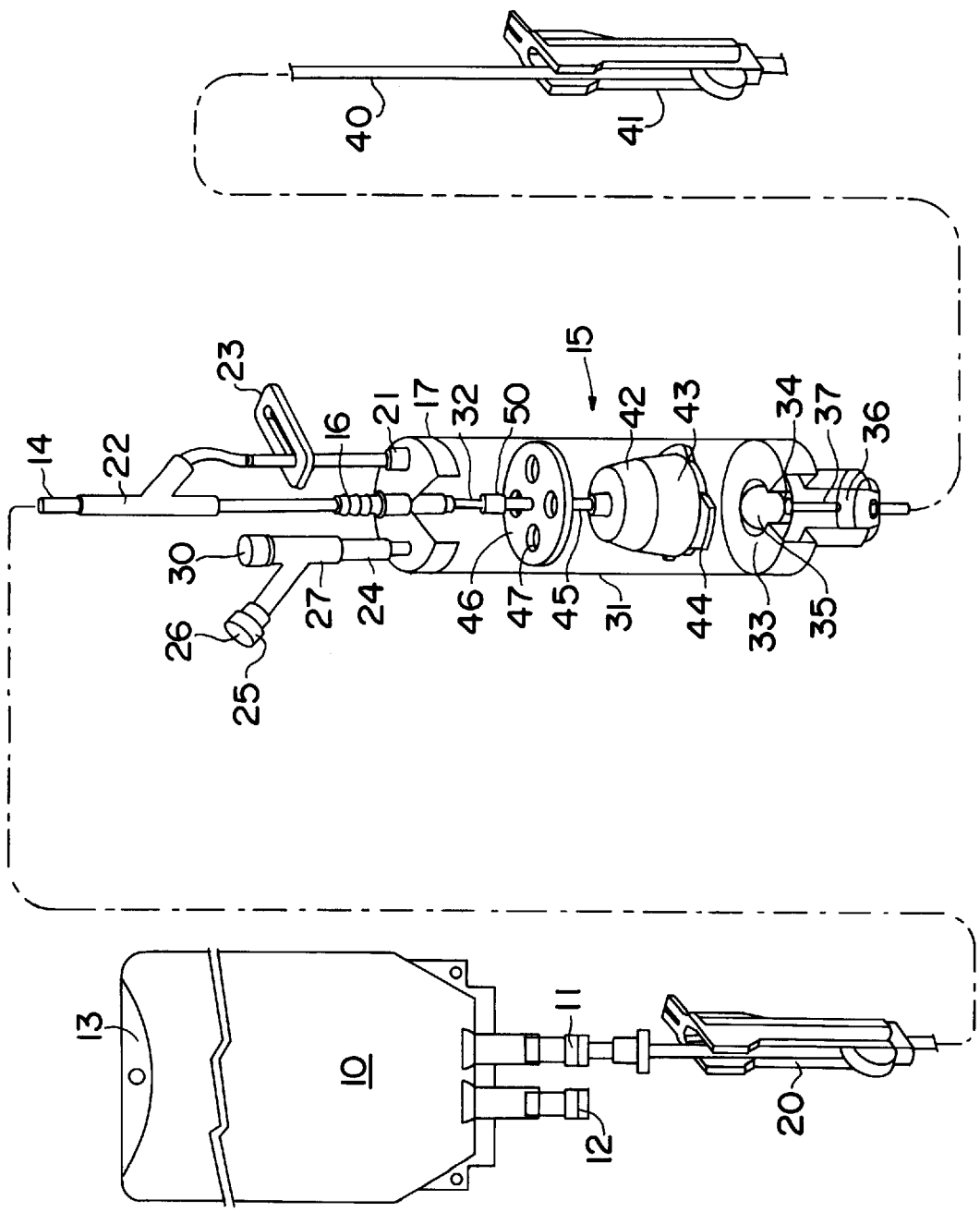

BURETTE APPARATUS

This invention relates to burette apparatus.

This invention has particular but not exclusive application to burette apparatus for administering intravenous (IV) liquids, and is described hereinafter in relation to this application. However, this invention may find use in other applications, such as metering systems in industry or the like.

Medical burettes are used to provide a reasonable precise flow rate from IV supplies to patients and to provide a means of introducing secondary fluids via a septum or the like. The precision of flow rate arises out of the isolation of the relatively short burette volume from the head of the IV source between fillings of the burette. Burettes uses to administer IV fluids generally comprise a graduated cylinder adapted to receive a selected volume of liquid from a collapsible container via a manually operable valve. The cylinder then delivers the IV fluid to a drip metering chamber providing a visual indication of flow rate, and thence to a selectively occludable drip line to the patient.

A disadvantage of the conventional system is that medical staff are required to periodically replenish the burette volume, which cannot be made so large as to introduce a substantial variation between flow rates between full and empty condition of the burette. In any case, the typical 100 ml burette must be of a diameter such that secondary additions may be measured in against the graduations of the burette. In practice this tends to introduce a head pressure difference between the full and low conditions that has an undesirable effect on flow rates between the two conditions.

The present invention aims to substantially alleviate at least one of the above disadvantages and to provide burette apparatus which will be reliable and efficient in use. Other objects and advantages of this invention will hereinafter become apparent.

With the foregoing and other objects in view, this invention in one aspect resides broadly in a burette apparatus including:
  a burette body member having an inlet connected to a source of liquid and an outlet;
  control means adapted to maintain the liquid level in said body member within a range;
  metering means for controlling the rate of flow of said liquid through said outlet, and
  closure means for said outlet operable at a minimum liquid level in said body member.

The burette body member may take any suitable form. For example, the body member may comprise a substantially transparent body member having its inlet in the region of the top and its outlet in the region of the bottom such that the fluid may be delivered by gravity. The body member may comprise a cylindrical portion adapted to be supported substantially vertically and upper and lower end closure portions including the inlet and outlet respectively.

The body member may be graduated such that the immediate liquid level therein may be determined. The body member may be provided with ancillary features such as secondary fluid injection points.

The inlet to the body member may include any suitable inlet assembly providing fluid connection to the liquid source. In the case of single use IV drip bags, the conventional delivery means for such fluids, the inlet assembly may include a flexible tube adapted to connect the burette inlet with the outlet of the bag, which is generally suspended in use above the burette. The inlet assembly may include vapour lock avoidance means, flow control valves and/or other conventional features of such assemblies.

The control means adapted to maintain the liquid level in said body member within a range may take the form of a condition responsive flow control assembly comprising a selectively operable closure means and operating means therefor, the operating means being responsive to the liquid level in the burette. For example, the control means may comprise an electronic level monitoring means and electromechanical valve means for selectively admitting said liquid.

Alternatively, the control means may comprise a float operated valve. For example, the control means may comprise a float located in said body member and adapted to operate a linear valve adapted to close the inlet upon a maximum fluid level being reached and to maintain the fluid level between that maximum and a minimum level. The linear valve may for example comprise a rubber or other resilient seat adapted to sealingly close an aperture providing fluid communication between the inlet and the interior of the body member. The seat may alternatively comprise a cup-like portion adapted to engage the aperture to provide sealing against the surface tension of a small quantity of liquid present in the cup. Preferably, the seat comprises a combination cup-shaped resilient seat to provide precise closure against the surface tension and positive closure against the resilient material.

The aperture advantageously comprises the end of a metal or other tube assembled to the end portion of the preferred cylindrical body member and forming part of the inlet assembly.

Preferably, the float, seat and tube end are mounted substantially coaxial with the preferred cylindrical burette body portion. The float may be provided with guide portions adapted to maintain the float in substantial concentricity with the preferred cylindrical body portion, whilst permitting the relatively free passage of fluid between the inlet and the body member when the control means so permits.

Preferably, the addition of secondary liquids to the body member causes the control means to close off flow until the level drops to the bottom of the range. The liquid level range controlled by the control means is preferably a minimum amount. For example, in apparatus adapted to replace a conventional 100 ml burette, the range may be 2 ml or even less, between for example 8 to 10 ml in the body member. By this means, variation in head pressure in the burette is substantially eliminated and the frequency of carer visits required is reduced simultaneously.

In order to provide for adequate secondary liquid volumes whilst operating over a narrow liquid level range for the primary liquid to reduce head variation, the body member preferably has a capacity in excess of said liquid level range to accommodate the secondary liquid addition. The float means may support the resilient seat atop a support member adapted to span the expected secondary liquid space, preferably extending coaxially with the cylindrical body portion. If desired the support means may take the form of a rod or the like and may also function as an upper guide for the float and rod assembly, when cooperating with complementary guide means associated with the body member.

The outlet for said body member may comprise an aperture allowing liquid to pass into a delivery tube or the like connected to a patient. Preferably, the outlet comprises an outlet assembly formed in an end closure portion of the body member.

The metering means for controlling the rate of flow of the liquid through the outlet may comprise a variable valve or limiting aperture or the like. Preferably, the metering means includes flow meter means whereby an indication of the flow rate may be given. For example, the metering means may comprise a variable clamp type valve disposed in a delivery line connected to the outlet, and used in conjunction with a visual drip indicator forming an outlet assembly with the end closure portion of the body member.

The closure means for said outlet may be operable to close off the flow by any suitable means responsive to the liquid level dropping below a predetermined minimum liquid level in the body member, such as when the liquid supply expires or is interrupted. The closure means may comprise a captive floating ball adapted to sealably engage a seat disposed across the outlet, the ball housing and seat advantageously being integrally formed in the outlet assembly comprising an end portion of the housing member.

Alternatively, in float operated apparatus, the closure means may comprise a sealing portion of the float adapted to sealingly engage the outlet when the float drops below a predetermined level. For example, the outlet may include a hollow tubular portion, preferably an extension of the preferred drip metering tube, extending up into the housing and adapted to sealably engage a resilient seat provided in the underside of the float.

Of course, the sealing arrangement may comprise a needle associated with the float and adapted to seal against a seat disposed about the outlet.

The burette body member head space may be vented or unvented. If the burette body member headspace is vented, it is preferably isolated from the atmosphere by communication with the preferably sterile headspace of the liquid supply container. In one embodiment, there is provided complementary connector means for joining the burette body member and a liquid supply reservoir. The connector portion associated with the burette body portion is provided with penetrating conduits adapted to penetrate single-use sealing members provided over aperture associated with the connector portion of the liquid supply container. Typically two such complementary pairs are provided in a one-way assembly connector one pair connecting the respective head spaces of the burette body and the liquid container and the other pair allowing communication of the fluid with the control means.

Apparatus as described above generally avoids flow variation by reducing the head variation in the burette to a minimum, without increasing nurse visits for refilling. However, in a further aspect, this invention includes embodiments where the metering means is adapted to provide a flow rate which is substantially independent of the actual physical head in the burette.

For example the metering means may comprise a float assembly including a variable aperture metering assembly configured such that at high heads the aperture allows substantially the same flow as at low heads. Such an arrangement may include, for example, a tapered needle adapted to pass into a metering tube and selected as to taper, length and relative dimensions to provide the requisite flow characteristic across the head range of a conventional burette or even a burette of greatly increased capacity.

In order that this invention may be more readily understood and put into practical effect, reference will now be made to the accompanying drawings which illustrate a preferred embodiment of the invention and wherein:

FIG. 1 is a partially cut away side view of apparatus in accordance with the present invention.

In the figure there is illustrated burette apparatus adapted for use with a conventional sterile liquid supply bag 10, having a delivery spigot 11 and a septum-covered injection spigot 12, and adapted to be suspended on an infusion stand by means of integrally formed suspension tag 13. A delivery tube 14 connects the delivery spigot 11 to a burette assembly 15, via a fluid entry spigot 16 formed in an end cap assembly 17 of the burette assembly 15. The delivery tube 14 is closable by a valve clamp 20.

The end cap assembly 17 is provided with a bypass spigot 21 adapted to be connected back to the delivery tube 14 at Y-piece 22, usually pressed closed by closure clip 23, to allow an override for adding liquid to the burette when the fluid entry spigot 16 is occluded as hereinafter described. The end cap assembly 17 is also provided with a utility spigot 24, in this example providing a sterile vent 25 though microporous cap 26, and an injection point 27 for secondary fluid through septum 30.

The end cap assembly 17 closes the upper end of a transparent, cylindrical burette body 31, into which extends a stainless steel tube extension 32 of the fluid entry spigot 16.

The lower end of the burette body 31 is closed by a lower closure assembly 33 comprising an integral ball housing and seat 34 containing a floating check ball 35, and being in fluid communication with a transparent drip chamber 36 via a stainless steel tube 37. An outlet tube 40 passes from the drip chamber 36 to the patient via regulating clamp 41.

A float assembly 42 is located in the burette body 31 and comprises a float body 43 having locating lugs 44 disposed about its periphery, and an extension rod 45 extending upwards, the extension rod 45 being constrained to the axis of the burette body 31 by guide plate 46. The guide plate 46 has passages 47 to permit free fluid passage thereby. The upper end of the extension rod 45 is provided with a resilient cup 50 adapted to engage the open end of the stainless steel tube extension 32.

In use, the bag 10 is fitted to the burette assembly 15 and the flow is commenced to purge the system. The cannula assembly (not shown) is purged in the usual manner and fitted to the patient. The regulating clamp is adjusted to the desired drip rate, as is the case with a conventional burette. As the fluid level drops in the burette assembly 15, the float body 43 also drops, pulling the cup 50 off the stainless steel tube extension 32. When the stainless steel tube extension 32 clears the maniscus of any fluid in the cup, the liquid can flow into the burette assembly 15 until the stainless steel tube extension 32 seals against the cup 50 again. In the present embodiment the range of volume in the apparatus is 2.5 ml to 11 ml, which, over the diameter of the burette body, represents very much less of a head variation than that imposed by the remaining components downstream such as the drip chamber 36. When the bag 10 empties, the float drops to the bottom of the burette assembly 15 and, as the liquid level passes down into the ball housing and seat 34, the floating check ball 35 seals the outlet to prevent air passing therethrough.

Apparatus in accordance with the foregoing embodiment has several particular advantages. By virtue of its operation as a closed system requiring a minimum of intervention, the apparatus is usable under a wide range of conditions generally considered as adverse for IV administration, such as underwater to SCUBA divers or in low gravity conditions. Since the apparatus is self regulating, the addition of secondary fluids via the side port septum does not affect the care regime insofar as nurse visits is concerned, since the apparatus will recommence primary fluid flow when the level of secondary fluid allows the float to pull the primary valve open. The apparatus is amenable to vented or unvented use.

It will of course be realised that while the above has been given by way of illustrative example of this invention, all such and other modifications and variations thereto as would be apparent to persons skilled in the art are deemed to fall within the broad scope and ambit of this invention as defined in the claims appended hereto.

We claim:

1. A burette apparatus comprising:

a burette body member having an inlet connected to a source of liquid and an outlet for allowing liquid to pass through the body;

control means for maintaining a liquid level in said body member, said control means comprising an inlet stub projecting into the body member from the inlet for directing the source of a liquid into the body, and a displaceable float assembly having a cup portion and a sealing fluid therein for stopping a liquid flow from the inlet stub when said inlet stub contacts the liquid of the cup;

metering means for controlling a rate flow of said liquid through said outlet; and outlet closure means operable at a minimum level of said liquid in said body member.

2. Burette apparatus according to claim 1, wherein said burette body member comprises a cylindrical portion supported substantially vertically, and upper and lower end closure portions including said inlet and outlet respectively.

3. Burette apparatus according to claim 2, wherein said upper end closure portion is provided with a secondary fluid injection point.

4. Burette apparatus according to claim 1, wherein said inlet to the body member comprises an inlet assembly providing fluid connection to a bag type liquid source via a flexible tube connecting the inlet with an outlet of the bag.

5. Burette apparatus according to claim 1, wherein said body member has a capacity in excess of said liquid level to accommodate secondary liquid addition.

6. Burette apparatus according to claim 5, wherein said cup portion comprises a rubber or other resilient seat closing said inlet when urged thereagainst by liquid in excess of said maximum level.

7. Burette apparatus according to claim 1, wherein said outlet comprises part of an outlet assembly formed in an end closure portion of the body member.

8. Burette apparatus according to claim 7, wherein said metering means comprises a variable valve or aperture.

9. Burette apparatus according to claim 7, wherein said outlet closure means is operable in response to the liquid level dropping below a predetermined minimum liquid level in the body member.

10. Burette apparatus according to claim 9, wherein said outlet closure means comprises a captive floating ball sealably engaging a seat disposed across the outlet.

11. Burette apparatus according to claim 9, wherein said outlet closure means comprises a sealing portion of said float sealingly engaging the outlet when the float drops below a predetermined level.

12. Burette apparatus according to claim 8, wherein said metering means for controlling the rate of flow of the liquid through the outlet comprises a variable clamp disposed on said delivery tube.

13. Burette apparatus according to claim 12, wherein said metering means includes flow meter means whereby an indication of the flow rate may be given.

14. Burette apparatus according to claim 13, wherein said flow meter means comprises a visual drip indicator forming part of said outlet assembly.

15. Burette apparatus according to claim 1, wherein a headspace in said body member is vented to the atmosphere.

16. Burette apparatus according to claim 1, wherein a headspace in said body member is vented to a corresponding headspace in said source of liquid.

17. Burette apparatus according to claim 16, wherein the connection between said liquid source and said inlet is made by means of complementary connector means including means providing for said headspace in said body member to vent to said corresponding headspace in said source of liquid.

18. Burette apparatus according to claim 1, wherein the connection between said liquid source and said inlet is made by means of complementary connector means including selectively operable bypass means enabling manually selective fluid flow into said body member.

* * * * *